United States Patent
Selig

(10) Patent No.: US 9,585,710 B2
(45) Date of Patent: Mar. 7, 2017

(54) METHOD FOR CONTROLLING AN ELECTRO-SURGICAL HF GENERATOR AND ELECTRO-SURGICAL DEVICE

(75) Inventor: Peter Selig, Hechingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 1427 days.

(21) Appl. No.: 12/812,883

(22) PCT Filed: Jan. 9, 2009

(86) PCT No.: PCT/EP2009/000088
§ 371 (c)(1),
(2), (4) Date: Jul. 14, 2010

(87) PCT Pub. No.: WO2009/090017
PCT Pub. Date: Jul. 23, 2009

(65) Prior Publication Data
US 2011/0054463 A1     Mar. 3, 2011

(30) Foreign Application Priority Data

Jan. 14, 2008  (DE) .................. 10 2008 004 241

(51) Int. Cl.
*A61B 18/12* (2006.01)
*A61B 18/00* (2006.01)
(52) U.S. Cl.
CPC *A61B 18/1206* (2013.01); *A61B 2018/00732* (2013.01)
(58) Field of Classification Search
CPC .............. A61B 5/02125; A61B 18/042; A61B 18/1206; A61B 18/1492; A61B 2017/00176; A61B 2017/00194; A61B 2018/00077; A61B 2018/1266; A61B 2018/1273
USPC ..................................... 606/34, 37
See application file for complete search history.

(56) References Cited

U.S. PATENT DOCUMENTS

| | | | |
|---|---|---|---|
| 3,898,991 A * | 8/1975 | Ikuno et al. | 606/37 |
| 4,154,240 A | 5/1979 | Ikuno et al. | |
| 4,211,230 A * | 7/1980 | Woltosz | 606/40 |
| 4,473,075 A | 9/1984 | Rexroth | |
| 5,318,563 A * | 6/1994 | Malis et al. | 606/38 |
| 5,488,627 A | 1/1996 | Hardin et al. | |
| 5,631,920 A * | 5/1997 | Hardin | 375/130 |
| 7,295,594 B1 * | 11/2007 | Lohr | H04B 15/04 |
| | | | 375/130 |
| 2002/0022836 A1 | 2/2002 | Goble et al. | |
| 2004/0097913 A1 * | 5/2004 | Refior et al. | 606/34 |
| 2004/0267333 A1 | 12/2004 | Kronberg | |
| 2007/0032827 A1 | 2/2007 | Katims | |
| 2007/0066971 A1 * | 3/2007 | Podhajsky | 606/34 |

OTHER PUBLICATIONS

K. B. Hardin et al., "Spread Spectrum Clock Generation for the Reduction of Radiated Emissions." IEEE, pp. 227-231, 1994.

* cited by examiner

*Primary Examiner* — Michael Peffley
*Assistant Examiner* — Khadijeh Vahdat
(74) *Attorney, Agent, or Firm* — Blank Rome LLP

(57) ABSTRACT

In an electro-surgical high-frequency generator, the signal frequency or the modulation frequency or a clock frequency or any combination thereof are modulated using a low-frequency modulation signal in such a way that the spectra thereof are widened. This results in a reduction of interference on peripheral devices.

20 Claims, 3 Drawing Sheets

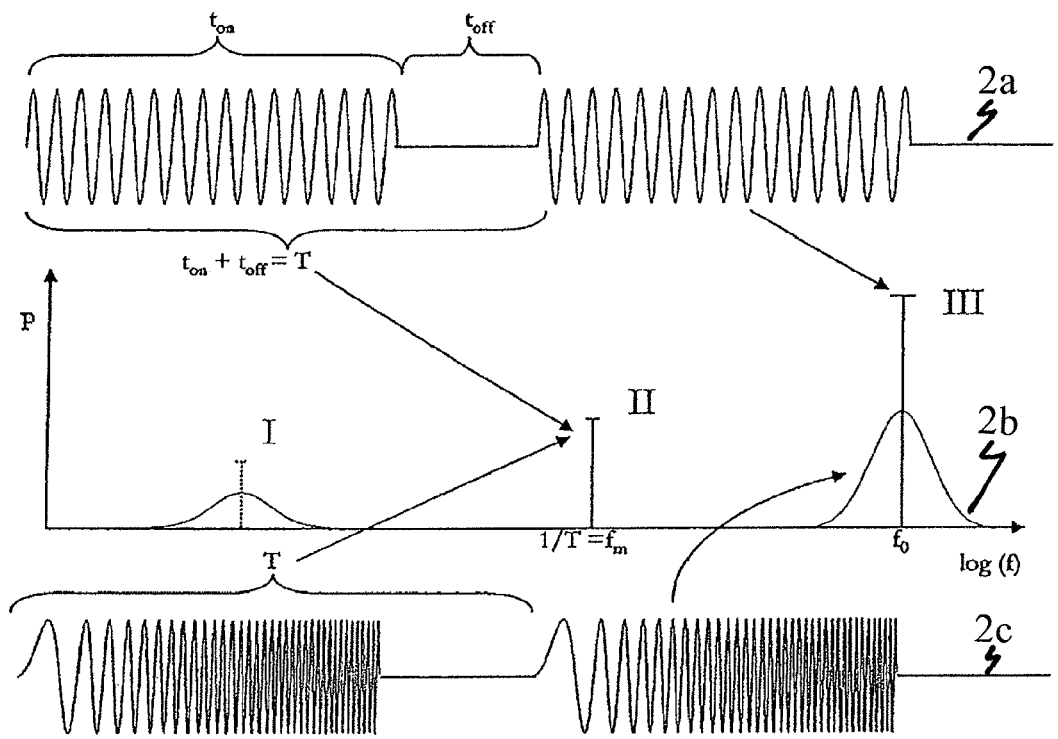
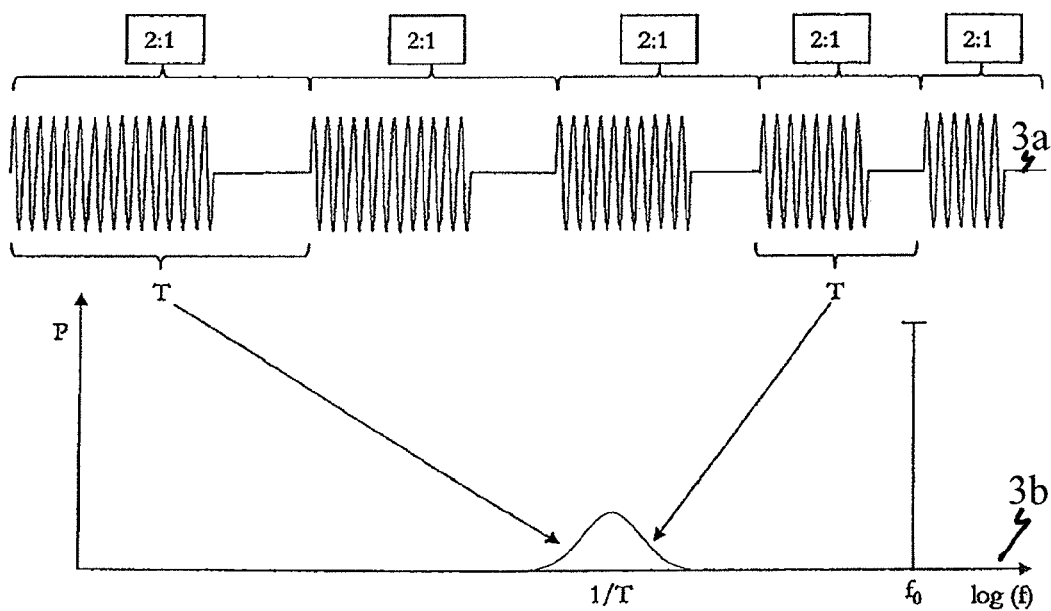

METHOD FOR CONTROLLING AN ELECTRO-SURGICAL HF GENERATOR AND ELECTRO-SURGICAL DEVICE

BACKGROUND OF THE INVENTION

The invention relates to a method for controlling an electro-surgical high-frequency ("HF") generator and an electro-surgical device.

Modern surgery frequently makes use of electro-surgical devices including a high-frequency generator for generating a high-frequency alternating current. This high-frequency alternating current is then used to cut or coagulate biological tissue or treat it in some other way.

The fundamental frequency of the HF generator is usually between 300 kHz and 4 MHz. Depending upon the application, this high-frequency is modulated in different ways with respect to its amplitudes. Usually, pulse duration modulation is performed in order to determine the power applied. Here, the ratio of burst-type signal segments to succeeding pauses is set. The clock frequency or modulation is usually performed with frequencies of between 1 kHz and 50 kHz.

In addition, further modulation (switching the output signal on and off) is performed with very low frequencies between 1 Hz and 10 Hz to achieve a power intensity which enables the operator to follow the progress of the treatment.

Finally, to avoid leakage currents or losses from the generators during idling with no load, very low-frequency pulses (e.g., sine beats of the fundamental frequency) are used.

In addition to electro-surgical devices, a plurality of other electrical or electronic devices is used in the operating theatre. These include, for example, patient monitoring devices (for example EEG devices) or video devices. A typical example of a video device essential for an operation is in operations performed using endoscopy. In this case, the video chip is located in the immediate vicinity of the location at which an electro-surgical instrument is used to apply the above-described high-frequency alternating current to tissue.

In all the above cases, there is frequently interference with the electronic device, which could even result in the failure of the patient monitor used meaning that, after a certain time, it is not possible to monitor the vital parameters of the patient. The same applies to the video picture. In all cases, problems of this kind can have fatal consequences for the patient.

BRIEF SUMMARY OF THE INVENTION

It is an object of the present invention, to disclose a method or an electro-surgical device with which interference, in particular on peripheral devices, is avoided or at least reduced.

In particular, the object is achieved by a method for controlling an electro-surgical HF generator, which generates a high-frequency output signal for treating, in particular, for cutting or coagulating biological tissue, wherein the HF generator is embodied in such a way that the output signal has a predetermined signal frequency and is generated continuously, modulated with a modulation frequency, or in bursts with a predetermined signal-to-pause pulse-duty ratio and a predetermined clock frequency. Here, the signal frequency and/or the modulation frequency and/or the clock frequency is modulated with a low-frequency modulation signal so that the spectra of signal frequency or modulation frequency or clock frequency are widened.

An essential point of invention is therefore the fact that, according to the present invention, the modulation frequency or clock frequency, but also the signal frequency, which was previously kept constant, are not kept at a constant value. With an observation in the frequency range, this results in a widening of the spectral lines (generated by constant frequencies) into spectral bands. This "frequency spread" results in greatly reduced peak values of the power, since the energy generated is not generated with one single frequency, but divided between a plurality of frequencies or a frequency band. This in turn achieves a significant reduction in both conducted and wireless interfering emissions, which has a favourable influence on the important EMC limit values of the device. This in turn results in a direct reduction in the electrical interference on patient monitors, video systems and other electrical or electronic devices with all the problematic consequences described. This additional modulation of the signals has no impact on the surgical effects, which are all very inert, since they are primarily based on thermal effects.

The modulation signal is preferably generated in a frequency range outside those frequencies which cause interference in peripheral medical devices, in particular in patient monitoring systems or patient monitoring or video systems. Here, despite the low signal energy, which contains the modulation frequency, as with the other modulation frequencies, it is therefore ensured that the action of interfering radiation is kept as low as possible.

The modulation signal preferably has a substantially constant course so that no sudden frequency changes and resulting interference signals (e.g., higher frequency signals) could occur.

The modulation signal can be embodied in different ways. It can be a preferably constantly sweeping signal so that the fundamental frequency and/or the clock frequency or the modulation frequency of the signal are changed continuously.

Another possibility is to embody the modulation signal as a random or noise signal.

It is also of advantage for the modulation signal to be set in a frequency range at or close to the system frequency. At this frequency, to be precise, the electronic devices used are usually equipped with effective blocking filters so that interference signals are suppressed in this range without any additional measures by filters that would be provided with the electronic devices.

The above object is achieved by a electro-surgical device with a high-frequency generator, which generates a high-frequency output signal for treating, in particular for cutting or coagulating, biological tissue, wherein the high-frequency generator is embodied in such a way that the output signal has a predetermined signal frequency and is generated continuously, modulated with a modulation frequency, or in bursts with a predetermined signal-to-pause pulse-duty ratio and a predetermined clock frequency. Here, a modulation generator is provided which generates a low-frequency modulation signal, which is supplied to the HF generator for controlling the output signal in such a way that the signal frequency and/or the modulation frequency and/or the clock frequency with the low-frequency modulation signal are modulated so that the spectra thereof are widened.

BRIEF DESCRIPTION OF THE DRAWINGS

The following describes an exemplary embodiment of the invention with reference to the identified figures.

FIGS. 2-4 illustrate different signal shapes with the associated spectra, according to embodiments of the invention.

DETAILED DESCRIPTION OF THE DISCLOSED EMBODIMENTS

Figure 1:
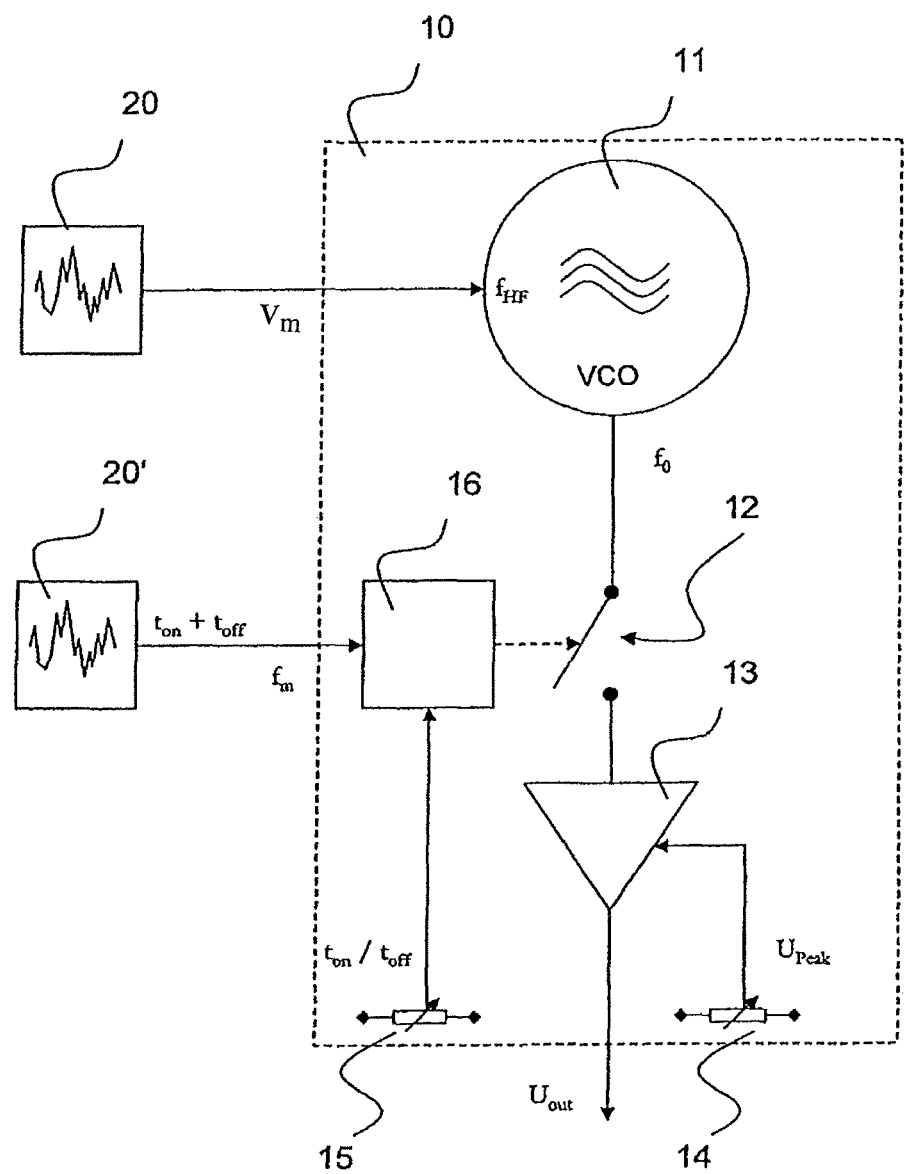
FIG. 1 is a block diagram of an embodiment of the electro-surgical device, according to embodiments of the invention.

In the following description, the same reference numerals denote the same parts or parts having similar functions.

FIG. 1 is a schematised drawing of an embodiment of an electro-surgical device according to the present invention. Details of this type of known electro-surgical device may be found, for example, in DE 199 43 792 C2, DE 100 46 592 C2, EP 0 430 929 B1 or EP 0 653 192 B1, to which express referral is made here, the specifications of which are incorporated by reference herein in their entirety.

An electro-surgical device of this kind comprises a high-frequency generator 10 which encompasses an oscillator 11, the output signal of which with the frequency $f_0$ is switched via a switch 12 and amplified by an output amplifier 13 so that an output signal $U_{out}$ is present at the output of the HF generator 10. Here, it is stressed that this is a schematic representation to explain the mode of operation of the arrangement.

To adjust the output amplitude $U_{peak}$, an adjusting device 14 is provided, which adjusts the amplification factor of the output amplifier 13. To control the switch 12, a switch control 16 is provided which adjusts the pulse-duty ratio via an adjusting device 15, that is the duration $t_{on}$, for which the output signal of the oscillator 11 is present at the input to the output amplifier 13, divided by the time $t_{off}$ during which the switch 12 is on.

The oscillator 11 is shown in the present example as VCO, indicating an oscillator, the oscillation frequency $f_{HF}$ of which can be controlled by a voltage $v_m$. This voltage $v_m$ is selected by a modulation generator 20.

The switch control 16 has a second input, via which a signal $t_{on}+t_{off}$ is received and processed so that the switch 12 is controlled with the predetermined pulse-duty ratio $t_{on}/t_{off}$ for the period $t_{on}+t_{off}$. This "period signal" represents a modulation signal with modulation frequency $f_m$, which is generated by a modulation generator 20'.

The following describes the mode of operation of this schematically depicted embodiment of the invention.

FIG. 2 shows the temporal course of a high-frequency signal with the frequency $f_0$ modulated by the switch 12 with a period $T=t_{on}+t_{off}$ (at reference 2a). The representation shown in reference 2b is a frequency spectrum in which the power P of the signal can be seen from the frequency (specifically, the logarithm of the frequency log(f)). The conventionally modulated high-frequency signal shown in reference 2a at frequency $f_0$ results, on the one hand, in a sharp spectral line, which is designated III in reference 2b. The modulation period T results in a spectral line at frequency $f_m$ (i.e., 1/T), which is designated II in reference 2b.

Reference 2b also shows another spectral line I, as described in the Background section above, which is in the very low-frequency range and originates from the signal modulation which is performed during "inactive" periods of use in order to keep the losses low.

Reference 2c shows a signal, which, according to the present invention, has, on the one hand, a constant modulation period T, but with which, on the other hand, the high-frequency signal is not present with a constant frequency $f_0$, but is swept. Therefore, the frequency rises over time and with each new period starts again at the lower frequency. This swept signal according to reference 2c results in the spectrum shown in reference 2b around the spectral line III, since lower frequency components and higher frequency components are present. However, when the modulation frequency for switching on and off of the signal is unchanged compared to reference 2a, the spectral line II in reference 2b is retained.

Reference 3a of FIG. 3 shows a signal with which the frequency $f_0$ of the high-frequency signal is unchanged. In addition, the signal according to reference 3a has a constant pulse-duty ratio $t_{on}/t_{off}=2/1$, wherein the periods T of individual signals consisting of a burst and a following pause vary in time. This results in a spectrum, as shown in reference 3b, in which the lower frequency 1/T, resulting from period T, appears as a spectrum, while the high-frequency signal generates a sharp spectral line at frequency $f_0$.

Figure 4:
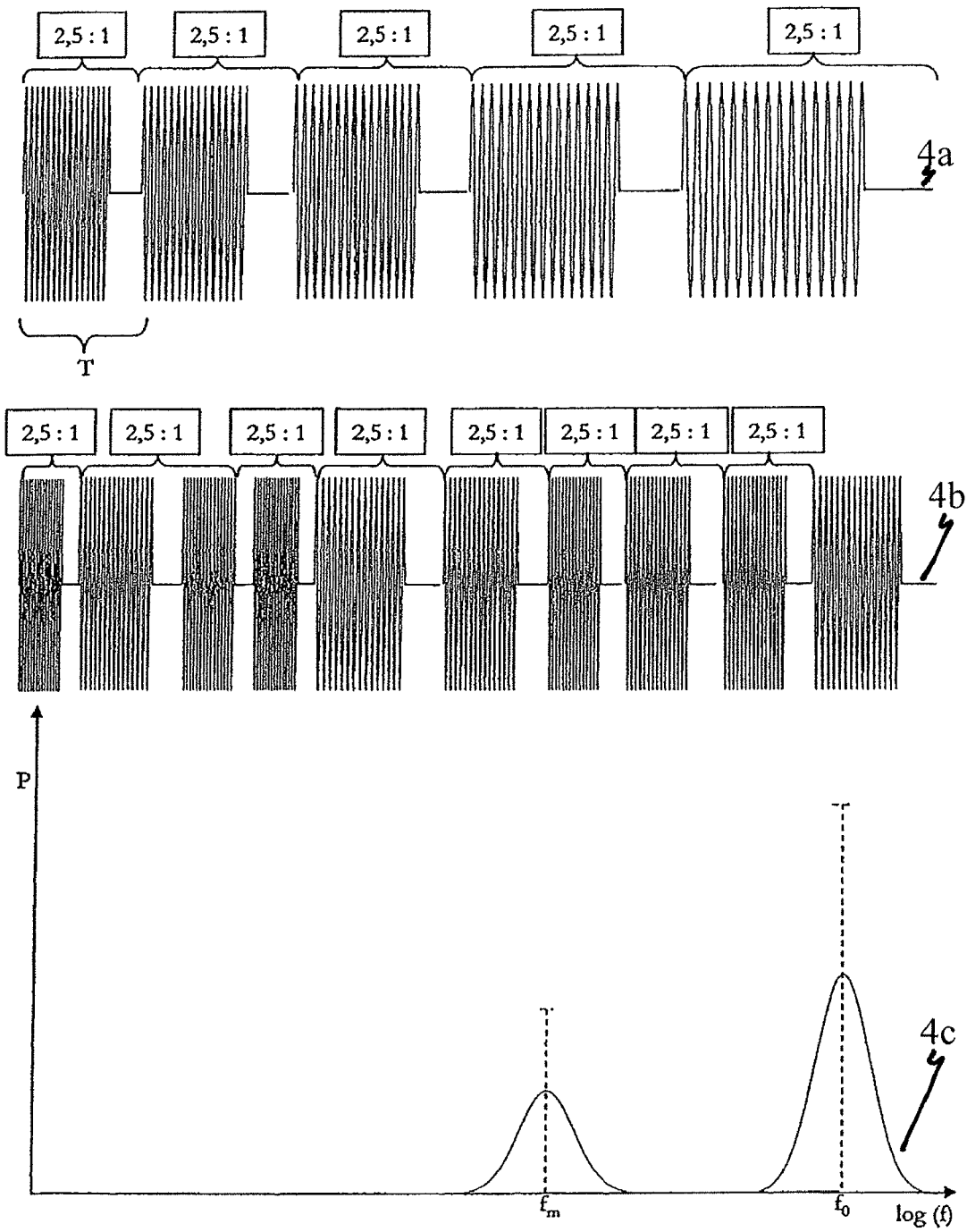

Reference 4a of FIG. 4 shows bursts with which the pulse-duty ratio is always $t_{on}/t_{off}=2.5/1$. The high-frequency signals within these bursts have a varying frequency. In addition, the periods T are different.

The signal course according to reference 4b differs from that in reference 4a in that the periods T do not rise continuously, but vary randomly. Otherwise, with the signal according to reference 4b, the pulse-duty ratio is again always 2.5/1.

These two signals shown in references 4a and 4b result in a spectrum as shown in reference 4c. Here, it is evident that the sharp spectral lines corresponding to the high-frequency signal or the modulations-clock frequency have disappeared and are replaced by broad spectra.

A comparison of the signal originating from a conventional electro-surgical generator according to reference 2a of FIG. 2 and the resulting spectrum according to reference 2b or reference 3c reveals that the maximum powers of sharp spectral lines, such as those obtained from continuous high-frequency signals or modulation with a constant frequency, fall significantly on the variation of the signal frequency or modulation frequency. This achieves the desired objective of greatly reducing the interfering radiation or the system-induced interference components which could have detrimental impacts on peripheral devices. Here, it is sufficient if the mean value of the frequencies of the HF signal or the modulation frequency only fluctuates by a few percent in order to achieve the described frequency spread, that is the expansion of individual spectral lines, into a widened spectrum.

This control of the signal or modulation frequency can be performed by the modulation generators 20 and 20' either regularly, for example with a sinusoidal signal or with any other type of signal, in particular with a noise signal. If the modulation is performed with a sinusoidal signal, a new spectral line (not shown in the figures) appears again in the output spectrum. If this spectral line is set so that it lies within a range that causes little interference to peripheral devices, for example at the system frequency, only low interference on the peripheral devices is to be expected since any interference to them is already usually suppressed in this frequency range. If the modulation generators 20, 20' modulate stochastically, once again an "interference spectrum" is generated, but, due to the above-described widening, its amplitude is very low. Here, once again, the centre frequency of the noise signal can advantageously be set in a range in which the peripheral devices to be protected from interference are "insensitive".

It may be derived from the above that an essential principle of the invention lies in the fact that periodic processes, that is the actual high-frequency signal and all modulation processes, which are used to generate special effects, are not kept constant but varied in time in order to avoid sharp spectral lines with high powers.

The invention claimed is:

1. A method for controlling an electro-surgical high-frequency generator whose output is for treating biological tissue by cutting or coagulating, said method comprising:
   using the high-frequency generator to generate a high-frequency output signal having a predetermined signal frequency, the high-frequency output signal either being generated continuously and modulated with a modulation frequency or being generated in bursts and having a constant signal-to-pause pulse-duty ratio and a predetermined clock frequency; and
   modulating the modulation frequency or the clock frequency with a low-frequency modulation signal so that frequency spectra thereof are widened.

2. The method according to claim 1, wherein the low-frequency modulation signal has a constant course.

3. The method according to claim 1, wherein the low-frequency modulation signal is a random or noise signal.

4. The method according to claim 1, wherein the low-frequency modulation signal is a constantly sweeping signal.

5. The method according to claim 1, wherein the modulating results in the modulation frequency or the clock frequency being varied less than 20%.

6. The method according to claim 5, wherein the modulating results in the modulation frequency or the clock frequency being varied less than 10%.

7. The method according to claim 6, wherein the modulating results in the modulation frequency or the clock frequency being varied less than 5%.

8. An electro-surgical device comprising:
   a high-frequency generator which generates a high-frequency output signal for treating biological tissue by cutting or coagulating, wherein the high-frequency generator is configured to output the high-frequency output signal with a predetermined signal frequency and to generate the high-frequency output signal continuously and modulated with a modulation frequency, or to generate the high-frequency output signal in bursts with a constant pulse-duty ratio of signal-to-pause and a predetermined clock frequency; and
   a modulation generator which generates a low-frequency modulation signal which is fed to the high-frequency generator for controlling the high-frequency output signal so that the modulation frequency or the clock frequency are modulated with the low-frequency modulation signal so that frequency spectra thereof are widened.

9. The electro-surgical device according to claim 8, wherein the low-frequency modulation signal has a constant course.

10. The electro-surgical device according to claim 9, wherein the low-frequency modulation signal is a random or noise signal.

11. The electro-surgical device according to claim 9, wherein the low-frequency modulation signal is a constantly sweeping signal.

12. The electro-surgical device according to claim 9, wherein the modulation frequency or the clock frequency are varied by less than 20%.

13. The electro-surgical device according to claim 8, wherein the low-frequency modulation signal is a random or noise signal.

14. The electro-surgical device according to claim 13, wherein the low-frequency modulation signal is a constantly sweeping signal.

15. The electro-surgical device according to claim 13, wherein the modulation frequency or the clock frequency are varied by less than 20%.

16. The electro-surgical device according to claim 8, wherein the low-frequency modulation signal is a constantly sweeping signal.

17. The electro-surgical device according to claim 16, wherein the modulation frequency or the clock frequency are varied by less than 20%.

18. The electro-surgical device according to claim 8, wherein the modulation frequency or the clock frequency are varied by less than 20%.

19. The electro-surgical device according to claim 18, wherein the modulation frequency or the clock frequency are varied by less than 10%.

20. The electro-surgical device according to claim 19, wherein the modulation frequency or the clock frequency are varied by less than 5%.

* * * * *